United States Patent
Aasberg-Petersen et al.

(10) Patent No.: US 10,889,496 B2
(45) Date of Patent: Jan. 12, 2021

(54) METHOD FOR THE PREPARATION OF SYNTHESIS GAS

(71) Applicant: Haldor Topsøe A/S, Kgs. Lyngby (DK)

(72) Inventors: Kim Aasberg-Petersen, Allerød (DK); Pat A. Han, Smørum (DK); Peter Mølgaard Mortensen, Roskilde (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 16/624,171

(22) PCT Filed: Jul. 20, 2018

(86) PCT No.: PCT/EP2018/069788
§ 371 (c)(1),
(2) Date: Dec. 18, 2019

(87) PCT Pub. No.: WO2019/020519
PCT Pub. Date: Jan. 31, 2019

(65) Prior Publication Data
US 2020/0140273 A1    May 7, 2020

(30) Foreign Application Priority Data

| Jul. 25, 2017 | (DK) | 2017 00425 |
| Sep. 25, 2017 | (DK) | 2017 00522 |
| May 28, 2018 | (DK) | 2018 00237 |
| Jul. 6, 2018 | (DK) | 2018 00345 |

(51) Int. Cl.
*C01B 3/32* (2006.01)
*C01B 3/38* (2006.01)
*C25B 1/04* (2006.01)
*C07C 31/04* (2006.01)

(52) U.S. Cl.
CPC .............. *C01B 3/382* (2013.01); *C01B 3/384* (2013.01); *C25B 1/04* (2013.01); *C01B 2203/0244* (2013.01); *C01B 2203/0844* (2013.01); *C07C 31/04* (2013.01)

(58) Field of Classification Search
None
See application file for complete search history.

(56) References Cited

U.S. PATENT DOCUMENTS

| 4,479,925 A | 10/1984 | Shires et al. |
| 4,792,441 A | 12/1988 | Wang et al. |
| 2004/0063798 A1 | 4/2004 | Erikstrup et al. |
| 2004/0182002 A1 | 9/2004 | Malhotra et al. |
| 2007/0256360 A1 | 11/2007 | Kindig et al. |
| 2009/0165459 A1 | 7/2009 | Henriksen et al. |
| 2010/0076097 A1 | 3/2010 | Metz et al. |
| 2012/0091730 A1 | 4/2012 | Stuermer et al. |
| 2013/0072583 A1 | 3/2013 | Koskinen et al. |
| 2013/0345325 A1 | 12/2013 | Lecomte et al. |
| 2014/0323597 A1 | 10/2014 | Stuckert et al. |

(Continued)

FOREIGN PATENT DOCUMENTS

| EP | 2 166 064 A1 | 3/2010 |
| EP | 2 589 574 A1 | 5/2013 |
| EP | 2 676 924 A1 | 12/2013 |

(Continued)

*Primary Examiner* — Medhanit W Bahta
(74) *Attorney, Agent, or Firm* — Blank Rome LLP

(57) ABSTRACT

Method for the preparation of synthesis gas by combining electrolysis of water, autothermal reforming and heat exchange reforming of a hydrocarbon feed stock.

6 Claims, 2 Drawing Sheets

(56) References Cited

U.S. PATENT DOCUMENTS

2016/0115405 A1    4/2016   Zubrin et al.
2017/0002281 A1    1/2017   Aasberg-Petersen et al.

FOREIGN PATENT DOCUMENTS

| EP | 2 805 914 B1 | 9/2017 |
|---|---|---|
| GB | 2545474 A | 6/2017 |
| KR | 10-2005-0075628 A | 7/2005 |
| WO | WO 2011/088981 A1 | 7/2011 |
| WO | WO 2012/084135 A1 | 6/2012 |
| WO | WO 2015/067436 A1 | 5/2015 |

METHOD FOR THE PREPARATION OF SYNTHESIS GAS

BACKGROUND OF THE INVENTION

1. Field of the Invention

The present application is directed to the preparation of synthesis gas. More particular, the invention combines electrolysis of water, autothermal reforming and heat exchange reforming of a hydrocarbon feed stock in the preparation of a hydrogen and carbon oxides containing synthesis gas.

2. Description of the Related Art

Production of synthesis gas e.g. for the methanol synthesis with natural gas feed is typically carried out by steam reforming.

The principal reaction of steam reforming is (given for methane):

$$CH_4 + H_2O \rightleftharpoons 3H_2 + CO$$

Steam reforming is normally accompanied by the water gas shift reaction:

$$CO + H_2O \rightleftharpoons CO_2 + H_2$$

Steam reforming can e.g. be done by, a combination of a tubular reformer (also called steam methane reformer, SMR) and autothermal reforming (ATR), also known as primary and secondary reforming or 2-step reforming. Alternatively, stand-alone SMR or stand-alone ATR can be used to prepare the synthesis gas.

The main elements of an ATR reactor are a burner, a combustion chamber, and a catalyst bed contained within a refractory lined pressure shell. In an ATR reactor, partial oxidation or combustion of a hydrocarbon feed by sub-stoichiometric amounts of oxygen is followed by steam reforming of the partially combusted hydrocarbon feed stream in a fixed bed of steam reforming catalyst. Steam reforming also takes place to some extent in the combustion chamber due to the high temperature. The steam reforming reaction is accompanied by the water gas shift reaction. Typically, the gas is at or close to equilibrium at the outlet of the ATR reactor with respect to steam reforming and water gas shift reactions. The temperature of the exit gas is typically in the range between 850 and 1100° C. More details of ATR and a full description can be found in the art such as "Studies in Surface Science and Catalysis, Vol. 152, "Synthesis gas production for FT synthesis"; Chapter 4, p. 258-352, 2004".

Regardless of whether stand-alone SMR, 2-step reforming, or stand-alone ATR is used, the product gas will comprise hydrogen, carbon monoxide, and carbon dioxide as well as other components normally including methane and steam.

Methanol synthesis gas has preferably a composition corresponding to a so-called module $(M=(H_2-O_2)/(CO+CO_2))$ of 1.90-2.20 or more preferably slightly above 2 (e.g., 2.00-2.10).

For standalone ATR, the module in the ATR exit gas is often lower than desired when the synthesis gas is used for methanol production. This can for example be rectified by removal of carbon dioxide or by recovering hydrogen from the purge gas from the methanol synthesis loop. In both cases, the methanol loop efficiency is lower than what is obtained if the synthesis gas for the methanol loop has a module slightly above 2 as discussed above.

Additionally, the ATR can be supplemented by a heat exchange reformer arranged either in series or in parallel with the ATR.

In the series solution, part or all the hydrocarbon feedstock is directed to the heat exchange reformer in which steam reforming takes place. The remaining part of the hydrocarbon feedstock may bypass the heat exchange reformer and be directed to the autothermal reformer. Typically, the gas leaving the heat exchange reformer in series will be at or close to equilibrium at a temperature of 650-800° C. The exit gas from the heat exchange reformer in series is then directed to the ATR together with any hydrocarbon feed which was not steam reformed in the heat exchange reformer. Part or all of the exit gas from the ATR is used as heat source in the heat exchange reformer by heat exchange to drive the endothermic steam reforming reaction.

In the parallel solution of the heat exchange reformer, part of the hydrocarbon feedstock is directed to the ATR and the remaining hydrocarbon feed stock and/or a second hydrocarbon feed stock to the heat exchange reformer.

The feed stocks to the ATR and to the heat exchange reformer may have different compositions, e.g. different steam to carbon ratios.

In the heat exchange reformer in the parallel concept steam reforming takes place. Part or all the exit gas from the ATR is utilized as heat source in the heat exchange reformer by heat exchange to drive the endothermic steam reforming reaction.

The gas leaving the catalyst in the heat exchange reformer may optionally be mixed with part or the entire the exit gas from the ATR before the latter is used as heat source. Alternatively, the exit gas from the heat exchange reformer and the exit gas from the ATR can be mixed downstream the heat exchange reformer.

A heat exchange reformer is alternatively called a gas heated reformer and heat exchange reforming may be called gas heated reforming.

SUMMARY OF THE INVENTION

We have found that when combining heat exchange reforming, ATR together with electrolysis of water and/or steam, the expensive ASU will be superfluous in the preparation of synthesis gas.

Thus, this invention provides a method for the preparation of synthesis gas comprising the steps of
(a) preparing a separate hydrogen containing stream and a separate oxygen containing stream by electrolysis of water and/or steam;
(b) providing a hydrocarbon feed stock;
(c1) steam reforming a part of the hydrocarbon feed stock from step (b) and/or a second hydrocarbon feedstock in indirect heat transfer relationship with part or all of an autothermal reformed gas leaving step (d) and mixing the heat exchange steam reformed gas stream with the autothermal reformed gas downstream step (d); or
(c2) heat exchange steam reforming a part or all of the hydrocarbon feed stock from step (b) in indirect heat transfer relationship with part or all of an autothermal reformed gas leaving step (d) to a heat exchange steam reformed gas and introducing the heat exchanged steam reformed gas into an autothermal reformer in step (d);
(d) providing in an autothermal reformer the autothermal reformed gas for use in step (c1) or step (c2) by autothermal reforming at least a part of the hydrocarbon feed stock from step (b) or at least a part of the heat exchange steam reformed gas from step (c2) with at least a part of the separate oxygen containing stream from step (a);
(e) introducing at least part of the separate hydrogen containing stream from step (a) into the mixed heat exchange reformed gas and autothermal reformed gas downstream step (c1) or into the autothermal reformed gas downstream step (c2) to obtain a synthesis gas comprising hydrogen, carbon monoxide and carbon dioxide; and
(f) withdrawing a synthesis gas.

DETAILED DESCRIPTION OF THE PREFERRED EMBODIMENTS

Figure 1:
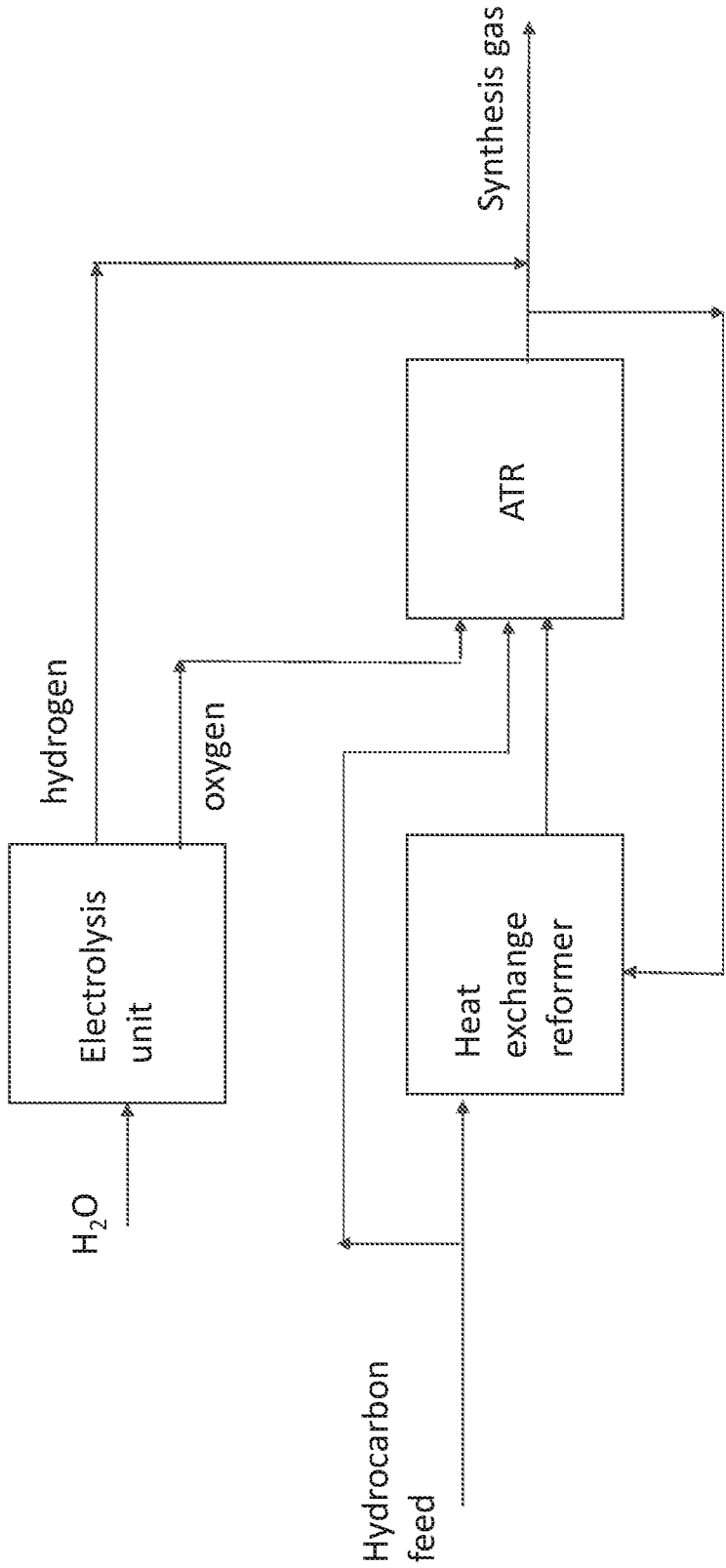
FIG. 1 shows a system for carrying out the method of the present invention, in which a heat exchange reformer is arranged in series with an ATR.

In the series heat exchange solution, shown in FIG. 1, part or all the hydrocarbon feedstock is directed to the heat exchange reformer in which steam reforming takes place. The remaining part of the hydrocarbon feedstock can bypass the heat exchange reformer and be directed to the autothermal reformer.

Typically, the gas leaving the heat exchange reformer in series will be at or close to equilibrium at a temperature of 550-800° C. The exit gas from the heat exchange reformer in series is then directed to the ATR. Part or all of the exit gas from the ATR is used as heat source in the heat exchange reformer by heat exchange to drive the endothermic steam reforming reaction.

Figure 2:
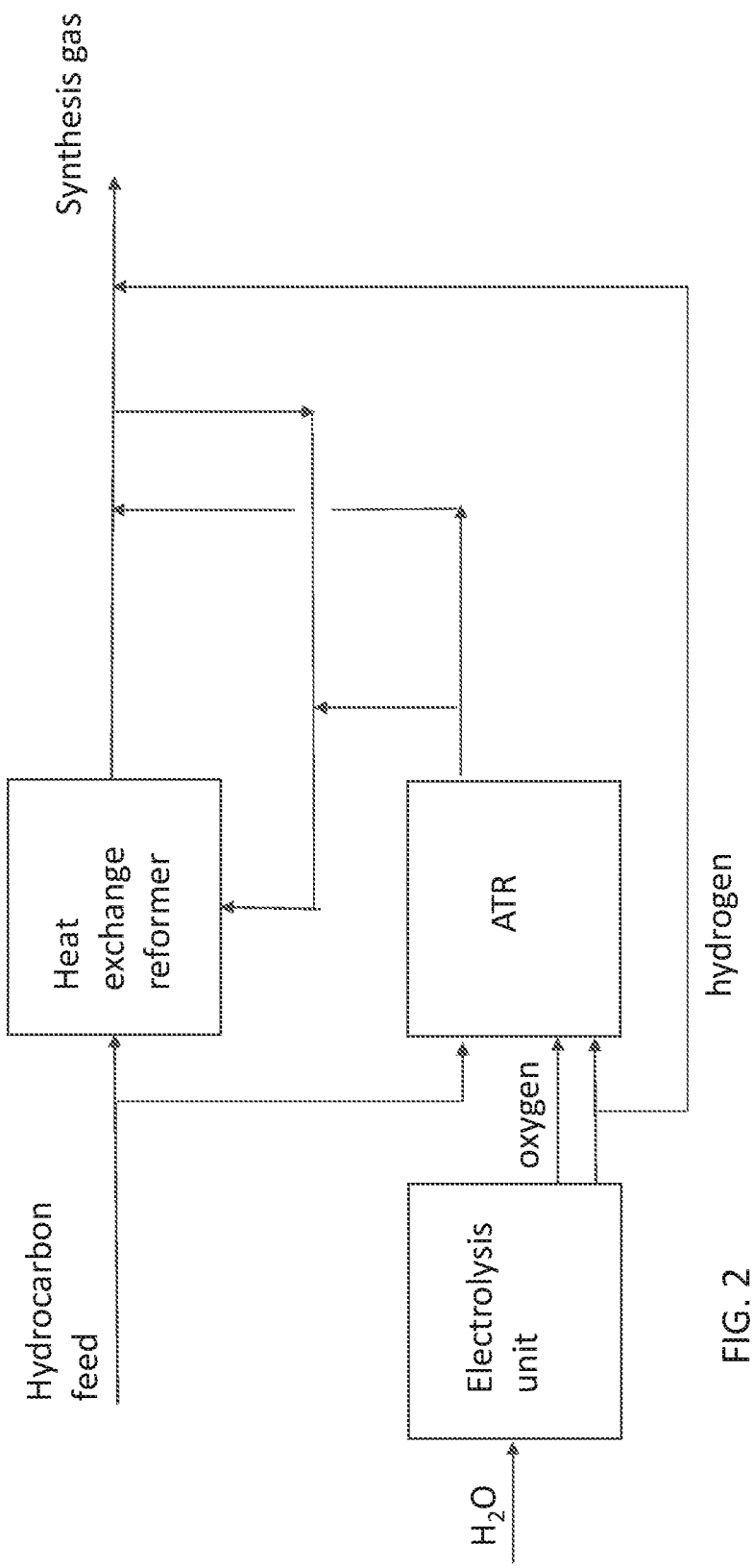
FIG. 2 shows a system for carrying out the method of the present invention, in which a heat exchange reformer is arranged in parallel with an ATR.

In the parallel solution of the heat exchange reformer, shown in FIG. 2, part of the hydrocarbon feedstock and/or a second hydrocarbon feedstock is directed to the ATR and the remaining hydrocarbon feed stock and/or a second hydrocarbon feed stock to the heat exchange reformer.

In the heat exchange reformer in the parallel concept part or all the exit gas from the ATR is utilized as heat source in the heat exchange reformer by heat exchange to drive the endothermic steam reforming reaction.

The gas leaving the catalyst in the heat exchange reformer may optionally be mixed with part or the entire the exit gas from the ATR before the latter is used as heat source. Alternatively, the exit gas from the heat exchange reformer and the exit gas from the ATR can be mixed downstream the heat exchange reformer.

The feed stocks to the ATR and to the heat exchange reformer may have different compositions, e.g different steam to carbon ratios.

Irrespective of whether a parallel or a series concept of the heat exchange reformer is used, the operating parameters, the amount of hydrogen from the electrolysis unit added in step (e) and the heat exchange reformer design can in principle be adjusted to give a module M of the desired value of 1.9-2.2 or preferably 2.0-2.1, in particular when using the synthesis gas for the preparation of methanol.

In general, the feed stock to the heat exchange reformer and ATR suitable for use in the invention comprises natural gas, methane, LNG, naphtha or mixtures thereof either as such or pre-reformed and/or desulfurized.

The amount of hydrogen addition can be tailored such that when the hydrogen is mixed with the process gas generated by the reforming steps, the desired value of M (between 1.90 and 2.20 or preferably between 2.00 and 2.10) is achieved.

In some cases, the amount of hydrogen from the electrolysis step may be too high to provide a module in the desired range. In this case part of the hydrogen may be used for other means.

Alternatively, the module can additionally be adjusted to the desired value by addition of essentially pure carbon dioxide to the hydrocarbon feed stock and/or to the synthesis gas, and/or upstream the autothermal reformer.

Thus, in an embodiment of the invention, essentially pure carbon dioxide is added to the hydrocarbon feed stock upstream of the autothermal reformer or downstream step (c1) or (c2) or downstream of step (d).

In all of the above cases, the feed stock may initially be subjected to the steps of purification (including desulphurization) and adiabatic pre-reforming as mentioned above.

The hydrocarbon feed stock may further comprise hydrogen and/or steam as well as other components.

The electrolysis can be performed by various means known in the art such as by solid oxide based electrolysis or electrolysis by alkaline cells or polymer cells (PEM).

If the power for the electrolysis is produced (at least in part) by sustainable sources, the CO2-emissions from the plant per unit of product produced is reduced.

The invention can further be employed for producing synthesis gas for other applications where it is desirable to increase the hydrogen concentration in the feed gas and where part of the oxygen needed for synthesis gas production is favorably produced by electrolysis.

The invention claimed is:
1. Method for the preparation of synthesis gas comprising the steps of:
(a) preparing a separate hydrogen containing stream and a separate oxygen containing stream by electrolysis of water and/or steam;
(b) providing a hydrocarbon feedstock;
(c1) steam reforming a part of the hydrocarbon feedstock from step (b), and/or a second hydrocarbon feedstock, by indirect heat transfer with part or all of an autothermal reformed gas leaving step (d), to obtain a steam reformed gas stream, and mixing the steam reformed gas stream with the autothermal reformed gas downstream of step (d); or
(c2) heat exchange steam reforming a part or all of the hydrocarbon feedstock from step (b), by indirect heat transfer with part or all of an autothermal reformed gas leaving step (d), to obtain a steam reformed gas, and introducing the steam reformed gas into an autothermal reformer in step (d) to obtain the autothermal reformed gas for use in step (c2);
(d) producing, as an exit gas in an autothermal reformer, the autothermal reformed gas for use in step (c1) or step (c2) by autothermal reforming a part of the hydrocarbon feedstock from step (b) or at least a part of the steam reformed gas from step (c2), with at least a part of the separate oxygen containing stream from step (a);
(e) introducing at least part of the separate hydrogen containing stream from step (a) into the mixed heat exchange reformed gas and autothermal reformed gas downstream step (c1) or into the autothermal reformed gas downstream step (d) to obtain a synthesis gas comprising hydrogen, carbon monoxide and carbon dioxide; and
(f) withdrawing a synthesis gas.

2. The method of claim 1, wherein carbon dioxide is added to the hydrocarbon feedstock upstream of the autothermal reformer or downstream step (c1) or (c2) or downstream of step (d).

3. The method of claim 2, wherein the carbon dioxide is added in an amount to provide a module ($M=(H_2-CO_2)/(CO+CO_2)$) in the synthesis gas prepared in step (d) in the range from 1.9-2.2.

4. The method of claim 1, wherein the hydrocarbon feedstock comprises natural gas, methane, LNG, naphtha or mixtures thereof either as such or pre-reformed and/or desulfurized.

5. The method of claim 1, wherein the electrolysis of water and/or steam in step (a) is powered at least in part by renewable energy.

6. The method of claim 1, wherein the synthesis gas prepared in step (f) is, in a further step, converted to a methanol product.

* * * * *